(12) United States Patent
Stollings (10) Patent No.: US 9,791,425 B2
(45) Date of Patent: Oct. 17, 2017

(54) SEMI-CONTINIOUS NON-METHANE ORGANIC CARBON ANALYZER (76) Inventor: Wayne Allen Stollings, Durham, NC (US)

( * ) Notice: Subject to any disclaimer, the term of this patent is extended or adjusted under 35 U.S.C. 154(b) by 415 days.

(21) Appl. No.: 13/616,542

(22) Filed: Sep. 14, 2012

(65) Prior Publication Data

US 2014/0080221 A1    Mar. 20, 2014

(51) Int. Cl.
*G01N 33/00* (2006.01)
*B01D 8/00* (2006.01)

(52) U.S. Cl.
CPC .......... *G01N 33/0016* (2013.01); *B01D 8/00* (2013.01); *G01N 33/0004* (2013.01); *G01N 33/0014* (2013.01); *G01N 33/0047* (2013.01); *G01N 2033/0019* (2013.01)

(58) Field of Classification Search
CPC ... G01N 33/0016; G01N 33/0004; B01D 8/00

USPC ................. 436/158; 62/55.5; 422/91, 90, 88
See application file for complete search history.

(56) References Cited

U.S. PATENT DOCUMENTS 5,349,833 A *  9/1994  Pardee et al. .................. 62/55.5
6,112,602 A *  9/2000  Mitra .......................... 73/863.12
6,295,836 B1 * 10/2001  Nguyen et al. ................. 62/643

* cited by examiner

*Primary Examiner* — Krishnan S Menon
*Assistant Examiner* — Dwan A Gerido (57) ABSTRACT

A filed portable analyzer capable of performing both the sampling and analytical procedures required by U.S. EPA Method 25 utilizing a small volume injection of sample onto a cryotrap cooled by a Stirling linear drive charged with helium to replace the field sampling condensate trap. The cryotrap is followed by the specified sorbent column/traps to ensure precise compatibility with prior reported compliance test results. The analytical system utilizes an oxidation catalyst and reduction catalyst to remove the potential for differing response factors on the FID from different compounds.

2 Claims, 8 Drawing Sheets

SEMI-CONTINIOUS NON-METHANE ORGANIC CARBON ANALYZER

BACKGROUND OF THE INVENTION

This invention relates to air pollution analyzers and the like which measure constituents in a sample gas stream. More particularly, the invention relates to a combination cryotrap and adsorbant traps used for extracting constituents from the sample gas stream.

Non-Methane Organic Compounds are defined in and by 40 CFR Appendix A Method 25. The historical data for this methodology therefore must be comparable to future data to ensure all of the data is legally defensible. Thus, any direct measurement systems must be able to be favorably compared with earlier non-directly measured analyses. The only proven method for this comparison is with a physical trapping procedure using cryogenic processes.

In a typical air pollution application, the air sample is passed through a cryotrap which is maintained at the temperature of dry ice. Heavier molecular weight constituents in the gas sample are condensed by the low temperature and solidify on the cold surfaces of the trap while lighter molecular weight constituents are separated or absorbed by the columns. After the desired amount of sample gas has passed through the trap, the gas flow path is changed so as to pass a carrier gas through the trap in place of the sample gas. At this time, the traps are heated. The frozen constituents vaporize, the absorbed constituents are desorbed, and both are carried away with the carrier gas to an analyzer or other instrument. The now clean traps are ready for another sampling and flushing cycle.

In the cryotraps commonly used, liquid nitrogen, liquid carbon dioxide, or solid dry ice are chosen for the freezing step. However, the coolant is lost to the atmosphere and a new quantity must be utilized for each operation. For instruments which operate continuously, the cost of these coolants is very high.

It is an object of the present invention to provide a new and improved cryotrap which uses a closed cycle cooler for the freezing, with no coolant being discharged after each sampling cycle. A further object of the invention is to provide such a cryotrap with a new and improved construction for obtaining increased efficiency in cooling and heating while enabling smaller construction and shorter operating cycles.

Earlier mechanical coolers are bulky, heavy, noisy, and have high mechanical vibration. They have relatively short life cycles or had long cycle times. The present invention is to use a Stirling closed cycle linear cooler which is relatively lightweight and compact. Features of the Stirling cooler include low conducted and radiated emissions, low mechanical vibration, acoustically quiet operation, and improved lifetime and reliability. The energy transfer is much greater and allows for a faster cooling cycle.

Other objects, advantages, features and results will more fully appear in the course of the following description.

SUMMARY OF THE INVENTION

The cryotrap of the invention includes a core having first means for receiving a cooling gas expander, a length of tubing carried on the core defining a gas flow path around the gas expander, where said tubing can be heated via electric resistance. The core preferably has a helical groove around the exterior thereof, with the tubing positioned in the groove. The core may be a cylindrical aluminum rod with a helical groove on the exterior with the tubing wound therein, and an axial opening for the gas expander.

The source of cooling may comprise a Stirling linear drive cooler charged with helium and having a gas compressor connected to one end of the gas expander with the other end of the expander positioned in the core.

Insulation for the cryotrap preferably includes a support for the core having a first central plate and a plurality of second insulator plates, with at least one second plate on each side of the first plate, and with the core positioned in the first plate. Each of the first and second plates is of a low density, closed cell, rigid foam thermal insulation with a plurality of openings therethrough, and metalized plastic film on each side of the plate, and includes crumpled metalized plastic film filling the openings of the second plate. A plurality of third insulator plates may be used with at least one third plate on each side of the first and second plate combination, and a fourth mounting plate on a side of the first, second and third plate combination with the plates joined in a sandwich construction.

DESCRIPTION OF THE PREFERRED EMBODIMENT

Figure 1:
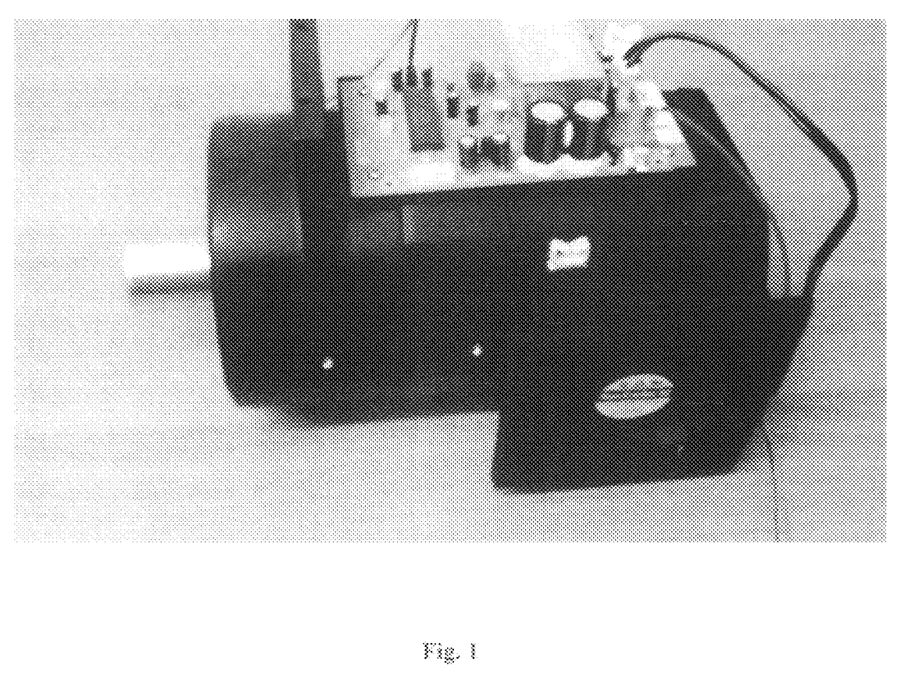
FIG. 1 is a view of a Stirling cooler assembly as used in the cryotrap.

In the cryotrap shown in FIG. 1, a core plate, apertured insulator plates, solid insulator plates, and a mounting plate are held together in a sandwich construction by rods and screws positioned at the corners of the plates. A core is positioned in the core plate and a gas expander is attached to the mounting plate by screws, with the tube of the gas expander extending through openings in the plates and into an axial opening in the core. A thermally conductive compound such as silver-loaded silicone grease may be applied to the end of the expander tube to improve the thermal connection to the core.

The gas expander is part of a refrigeration system which provides for cooling of the core. In the preferred embodiment illustrated, a Stirling linear cooler is utilized, having a compressor connected to the gas expander. The Stirling linear cooler may be of conventional design, providing a closed cycle with helium being compressed at the compressor and with pressure pulses transferred through the helium to the expander. Cooling is obtained by cyclic out-of-phase motion of a compression piston and a displacer-regenerator located in the expander assembly. The compressor is operated for a time prior to the introduction of the sample to allow the core and tubing to reach the desired operating temperature. The compressor continues to operate during the time that the sample is passed through the trap tubing. The compressor is then turned off during the heating mode.

Figure 2:
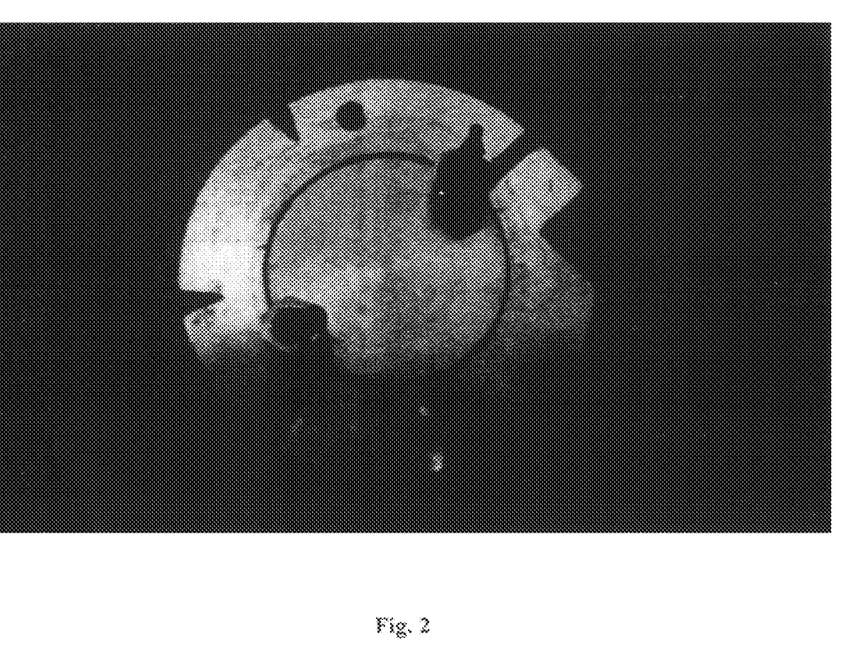
FIG. 2 is a view of the core and coil in the assembly of the cryotrap of FIG. 4.

The core preferably is a aluminum disc with a helical groove on the exterior. A length of tubing, preferably of stainless steel, is wound on the core in the helical groove. Temperature sensor may be positioned in openings in the core, preferably between the gas expander opening and the helical groove. The temperature sensor is connected to a control circuit by wires.

The stainless steel tubing of the trap is heated via the electrical resistance of a DC current passing from one end through the other.

Figure 3:
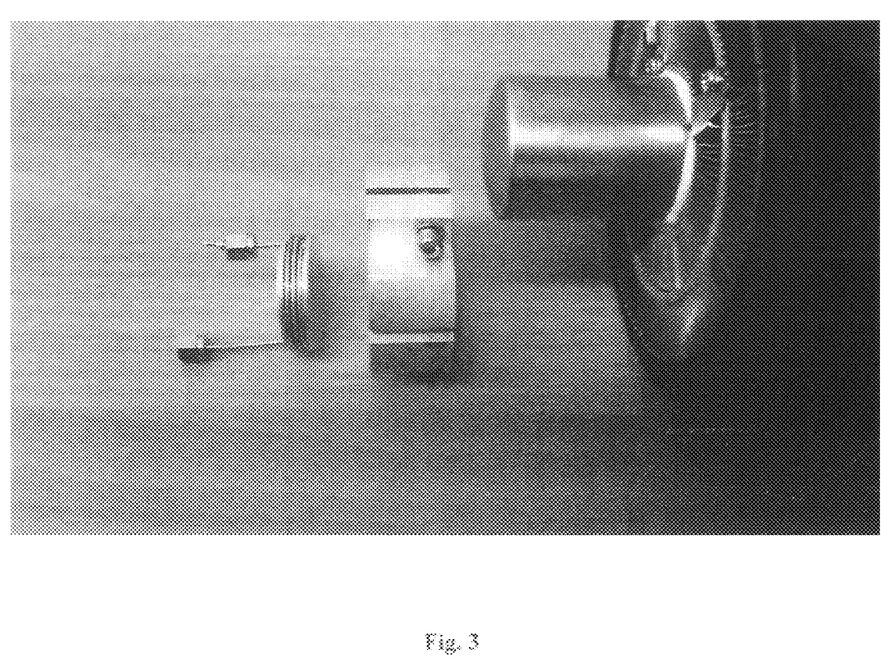
FIG. 3 is an exploded view of the main components of the cryotrap incorporating the presently preferred embodiment of the invention.
Figure 4:
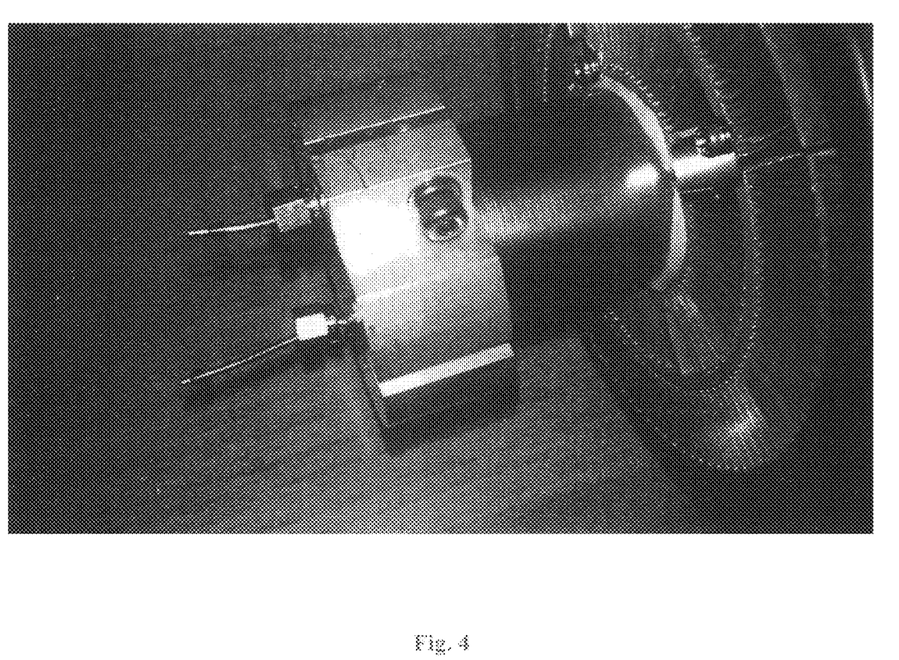
FIG. 4 is a view of the assembly of the main components of the cryotrap; coil, core, collar and Stirling cooler.

During the cooling modes, the compressor control electronics hold the core temperature to a selectable preset temperature as sensed by the temperature sensor. The heater temperature controller also provides a display of the core temperature. Cooling and heating modes are controlled by the cryotrap sequence control electronics, with power from a DC power supply. Desirably, the core plate and insulator plates are formed of a low density, closed cell, rigid foam for thermal insulation, typically a polymethacrylimide foam. The individual plates preferably are about ½" thick and about 4" square. A layer of moralized plastic film, typically aluminized Mylar film, is positioned on each side of each plate, typically about 0.0005" thick.

A plurality of openings are provided in each of the core plate and insulator plates, typically about ½" in diameter. Prior to applying the surface layers, the openings preferably are filled with crumpled metalized plastic film, typically aluminized Mylar film. Also, preferably the openings in adjacent plates are misaligned.

In operation, the core is cooled by the gas expander rod in the opening of the core. Substantial insulation is provided around the core and the gas expander tube so there is minimal heating from the surrounding atmosphere. At the same time, heat is periodically applied to the tubing for thawing the frozen gas constituents. It has been found that the insulation construction using the foam plates, with the crumpled metalized film in the openings achieves an excellent balance between heating and cooling, permitting freezing of substantially all constituents in the gas while at the same time requiring a minimum of cooling energy and permitting a rapid cycle tune.

It is desirable to cool the core quickly. Rapid cooling minimizes wear on the Stirling cooler and enables the cryotrap to complete a cooling/heating cycle quickly. To cool the core quickly it is necessary to minimize the amount of material that must be cooled. This includes the insulating material around the core, therefore insulating material is removed resulting in a plurality of openings in each of the core plates and insulator plates. The openings are typically ½" in diameter leaving a "web" of foam insulation to support the core and providing a longer path through the foam from the core to the outside. To prevent air currents from circulating in these openings, the openings are filled with crumpled metalized plastic film, typically aluminized Mylar film. Metalized plastic film is also bonded to each side of the insulating plate. The metalized plastic film also serves to reflect external radiant energy away from the core.

Figure 5A:
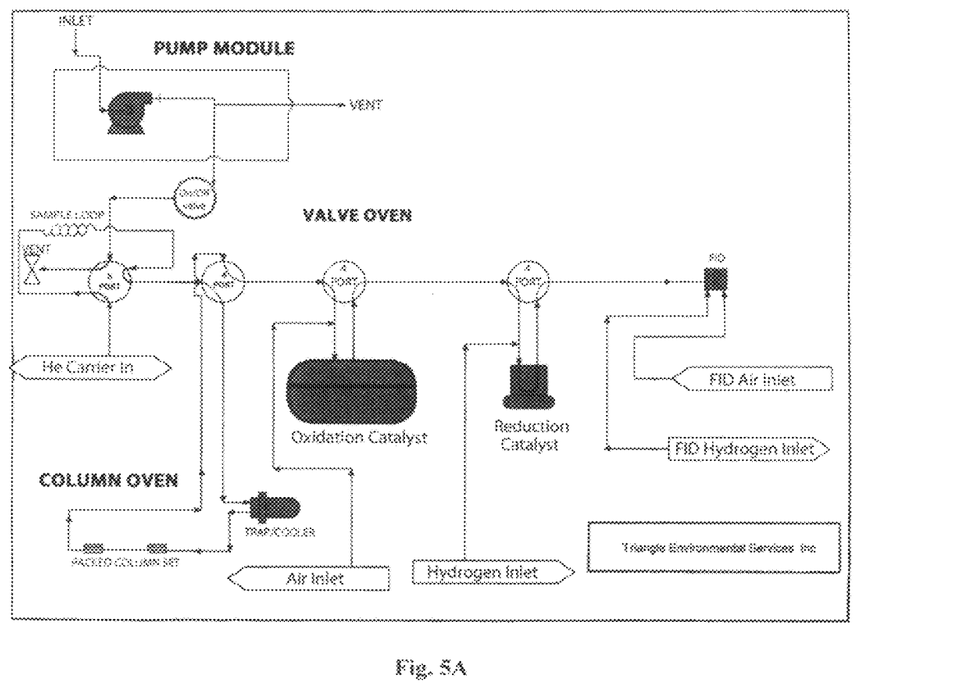
FIG. 5A showing the plumbing pathways through the system using a 4 and 6 port combination.
Figure 5B:
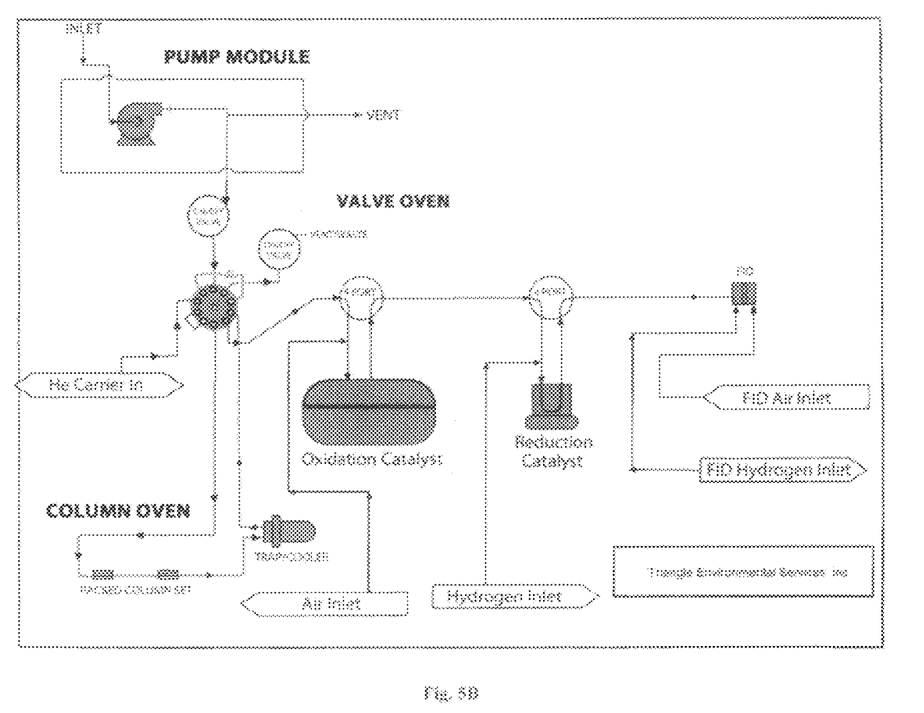
FIG. 5B is a diagram illustrating the operation of the cryotrap, with a 10 port control valve in the sampling position showing the two flow paths through the valve.
Figure 5C:
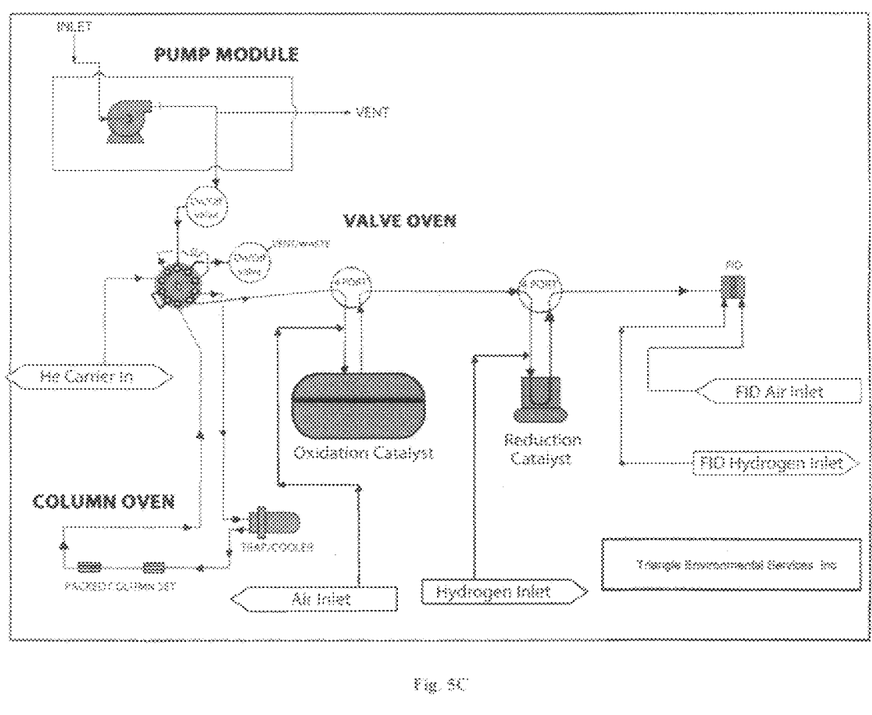
FIG. 5C is a diagram similar to that of FIG. 5A with a 10 port control valve in the injecting position showing helium carrier flow to the detector.
Figure 5D:
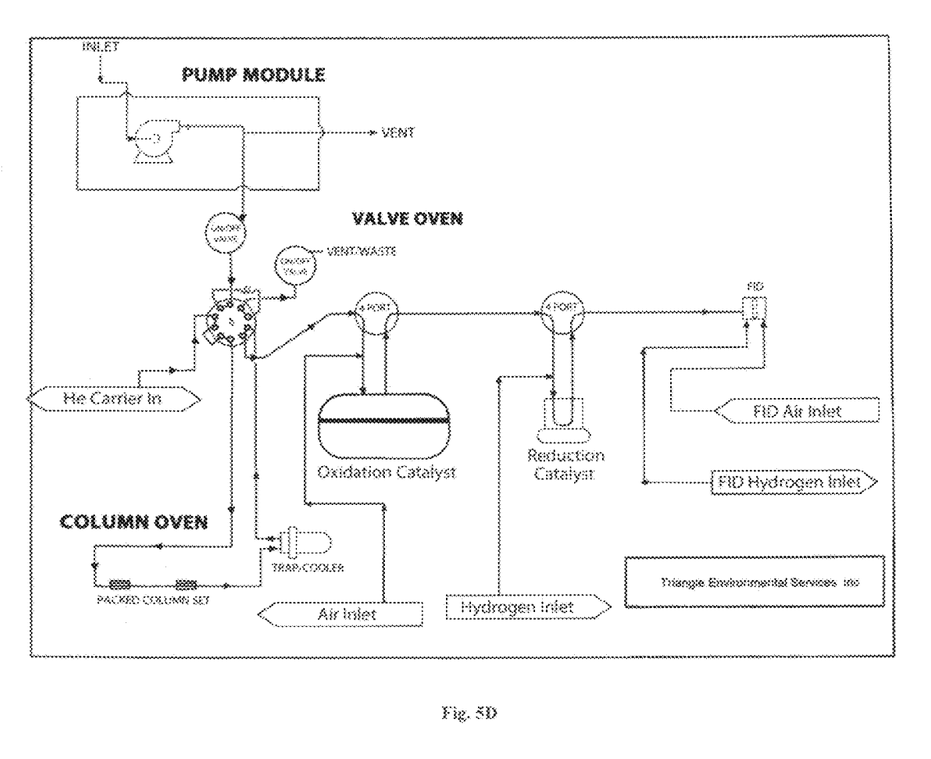
FIG. 5D is a diagram similar to that of FIG. 5C showing the flow of helium carrier to the detector with the valve in the backflush position.

The cryotrap is utilized with a ten port valve which is movable between a sampling position shown in FIG. 5B and a flushing position shown in FIGS. 5C and 5D. A source of sample gas is connected to the valve through a line, and a vent for the sample gas is connected to the valve through another line. The carrier gas from an analyzer such as a gas chromatograph is connected to the valve by an incoming line and an outgoing line. The tubing is connected to the valve.

During the sampling mode, the sample gas flows through the line, the valve, through the tubing, and back through the valve to the vent line, with the carrier gas flowing directly to and from the valve to the detector.

With the valve turned to the flushing mode, the sample gas flows directly into and out of the valve, with the carrier gas flowing through the line to the valve, through the tubing and back to the analyzer through the valve and the line.

The operation of the valve may be automatic, operating on a predetermined cycle or may be manually operated as desired.

If a faster analytical cycle is desired, a second cryotrap assembly may be added along with a 6 port valve to switch between traps. In such a case one trap would be cooling while the other is used for the sampling and analysis.

REFERENCES

Mitra S., Yun C. "Continuous gas chromatographic monitoring of low concentration sample streams using an on-line microtrap" J. Chromatogr. A 648, 415-421 (1993)

Feng C. H., Mitra S. "Two-stage microtrap as an injection device for continuous on-line gas chromatographic monitoring" J. Chromatogr. A805, 169-176 (1998)

Mita S. "Analytical apparatus and instrumentation for on-line measurement of volatile organic compounds in fluids" U.S. Pat. No. 6,112,602 Sep. 5, (2000)

40 CFR 60. Appendix A to Part 60 Method 25—Determination of total gaseous non-methane organic emissions as carbon US Patent References U.S. Pat. No. 4,148,196, Apr. 10, 1979, French, et al., Multiple stage cryogenic pump and method of pumping U.S. Pat. No. 4,283,948, Aug. 18, 1981, Longsworth, Cryogenic air sampler U.S. Pat. No. 4,479,927, Oct. 30, 1984, Gelemt, Regenerable cold trap for aluminum chloride effluent U.S. Pat. No. 4,506,513, Mar. 26, 1985, Max, Cold trap U.S. Pat. No. 4,607,491, Aug. 26, 1986, Ishimaru, et al., Cooling trap for vacuum U.S. Pat. No. 5,073,896, Dec. 17, 1991, Reid, et al., Purification of laser gases U.S. Pat. No. 5,349,833, Sep. 27, 1994, Pardee, et al., Cryotrap for air pollution analyzer U.S. Pat. No. 5,537,833, Jul. 23, 1996, Matte, et al., Shielded cryogenic trap U.S. Pat. No. 5,596,876, Jan. 28, 1997, Manura, et al., Miniaturized cryogenic trap apparatus U.S. Pat. No. 6,477,905, Nov. 12, 2002, Mitra, Apparatus and instrumentation for measurement of TOC, NMOC and VOCs U.S. Pat. No. 7,370,482, May 13, 2008, Desbiolles, et al, Rapidly regenerating cryogenic trap U.S. Pat. No. 8,127,595, Mar. 6, 2012, Finlay, et al., Pre-concentrator and sample interface

The invention claimed is:

1. A device for measurement of Non-Methane Organic Carbons (NMOCs) including Volatile Organic Carbons (VOC's) in a sample stream without chromatographic separation of the NMOC's comprising a sample inlet for introducing a sample into the device a carrier inlet for introducing a carrier gas into the device a sampling and concentration system within said device, the sampling and concentration system comprising a cryotrap capable of rapid heating and cooling wherein said cryotrap removes heavy organic compounds from the sample stream an adsorbent trap capable of rapid heating and cooling wherein said adsorbent trap removes light organic compounds from the sample stream one or more multi-port valves in fluid communication with the cryotrap and the adsorbent trap to allow separation of carbon monoxide, carbon dioxide, and methane in the sample stream, thereby concentrating NMOC's and VOC's in said traps an oxidation catalyst downstream of the cryotrap and adsorbent trap wherein the oxidation catalyst converts NMOC's and VOC's to carbon dioxide a reduction catalyst downstream of the oxidation catalyst wherein the reduction catalyst converts carbon dioxide to methane and a detector to measure NMOC's and VOC's in the sample stream wherein the detector is selected from the group consisting of a flame ionization detector (FID) or an infrared spectrometer.

2. A device according to claim 1 wherein the multi-port valves comprise four, six, or ten port valves operating simultaneously with the trap.

* * * * *